(12) United States Patent
Zhang et al.

(10) Patent No.: US 12,263,034 B2
(45) Date of Patent: Apr. 1, 2025

(54) ULTRASONIC METHOD FOR QUANTIFYING THE NONLINEAR SHEAR WAVE ELASTICITY OF A MEDIUM, AND DEVICE FOR IMPLEMENTING THIS METHOD

(71) Applicant: SUPERSONIC IMAGINE, Aix-en-Provence (FR)

(72) Inventors: Bo Zhang, Cabries (FR); Ling Tong, Aix-en-Provence (FR); Cyril Dolgoff, Ginasservis (FR); Hélène Sportouche, Marseilles (FR); Jean-Pierre Henry, Marseilles (FR)

(73) Assignee: SUPERSONIC IMAGINE, Aix-en-Provence (FR)

( * ) Notice: Subject to any disclaimer, the term of this patent is extended or adjusted under 35 U.S.C. 154(b) by 250 days.

(21) Appl. No.: 17/784,050

(22) PCT Filed: Dec. 10, 2020

(86) PCT No.: PCT/EP2020/085606
§ 371 (c)(1),
(2) Date: Jun. 9, 2022

(87) PCT Pub. No.: WO2021/116326
PCT Pub. Date: Jun. 17, 2021

(65) Prior Publication Data
US 2023/0026896 A1 Jan. 26, 2023

(30) Foreign Application Priority Data
Dec. 13, 2019 (FR) ........................... 1914432

(51) Int. Cl.
*A61B 8/08* (2006.01)
*A61B 8/00* (2006.01)
*G01S 7/52* (2006.01)

(52) U.S. Cl.
CPC .............. *A61B 8/085* (2013.01); *A61B 8/463* (2013.01); *A61B 8/485* (2013.01);
(Continued)

(58) Field of Classification Search
CPC ......... A61B 8/085; A61B 8/463; A61B 8/485; G01S 7/52022; G01S 7/52042; G01S 7/52073
See application file for complete search history.

(56) References Cited

U.S. PATENT DOCUMENTS

| | | |
|---|---|---|
| 2005/0252295 A1 | 11/2005 | Fink et al. |
| 2006/0285731 A1 | 12/2006 | Jiang et al. |

(Continued)

FOREIGN PATENT DOCUMENTS

| | | |
|---|---|---|
| CN | 101912278 A | 12/2010 |
| JP | 2007-282932 | 11/2007 |

(Continued)

OTHER PUBLICATIONS

Bernal et al., "In Vivo Quantification of the Nonlinear Shear Modulus in Breast Lesions: Feasibility Study", IEEE Trans Ultrason Ferroelectr Freq Control, Jan. 2016; 63(1): 101-9.

(Continued)

*Primary Examiner* — Dixomara Vargas
(74) *Attorney, Agent, or Firm* — Merchant & Gould P.C.

(57) ABSTRACT

An ultrasonic method for quantifying the nonlinear shear wave elasticity of a medium, the method comprising the following steps:
  A1.—collecting a temporal succession of shear wave elasticity data from the medium,
  A2.—applying, to the medium, a deformation that successively changes according to a predetermined sequence of deformations, during the collection of the shear waves, (Continued)

A3.—observing the actual evolution of deformation, and

B.—quantifying the nonlinear elasticity of the medium depending on the temporal succession of data and the evolution of deformation.

22 Claims, 4 Drawing Sheets

(52) U.S. Cl.
CPC ...... *G01S 7/52022* (2013.01); *G01S 7/52042* (2013.01); *G01S 7/52073* (2013.01)

(56) References Cited

U.S. PATENT DOCUMENTS

| | | | |
|---|---|---|---|
| 2007/0093716 A1* | 4/2007 | Radulescu | G01S 7/5206 600/437 |
| 2009/0234230 A1 | 9/2009 | Bercoff et al. | |
| 2010/0312116 A1* | 12/2010 | Pernot | G01N 29/11 600/453 |
| 2011/0028838 A1* | 2/2011 | Pernot | G01N 29/0672 600/437 |
| 2011/0054314 A1 | 3/2011 | Tanigawa et al. | |
| 2014/0148698 A1* | 5/2014 | Tamano | G01S 7/52042 600/438 |
| 2016/0213341 A1* | 7/2016 | Salcudean | A61B 6/50 |
| 2017/0340310 A1* | 11/2017 | Carlini | G01S 7/52022 |
| 2017/0343656 A1 | 11/2017 | Angelsen | |
| 2018/0140279 A1* | 5/2018 | Perrey | A61B 8/5223 |
| 2019/0231317 A1* | 8/2019 | Anthony | A61B 8/429 |
| 2019/0254639 A1* | 8/2019 | Yin | A61B 8/085 |
| 2019/0328364 A1* | 10/2019 | Questa | G01S 7/52042 |
| 2019/0350559 A1* | 11/2019 | Bini | A61B 8/485 |
| 2020/0060654 A1* | 2/2020 | Nguyen | G01S 7/52042 |
| 2020/0085407 A1* | 3/2020 | Grundfest | A61B 8/085 |
| 2022/0104794 A1* | 4/2022 | De Beni | G06N 20/00 |
| 2022/0222787 A1* | 7/2022 | Couade | G06T 3/60 |
| 2023/0044531 A1* | 2/2023 | Etaix | G01N 29/07 |

FOREIGN PATENT DOCUMENTS

| | | |
|---|---|---|
| JP | 2009-201989 | 9/2009 |
| JP | 2010-017585 | 1/2010 |
| JP | 2013-500752 | 1/2013 |
| JP | 2013-034883 | 2/2013 |
| JP | 2013-158348 | 8/2013 |
| JP | 2015-058193 | 3/2015 |
| WO | 2007/083745 | 7/2007 |
| WO | 2018/051265 | 3/2018 |

OTHER PUBLICATIONS

Bouget, J-Y, "Pyramidal Implementation of the Lucas Kanade Feature Tracker: Description of the Algorithm", Intel Corp., 1999, 9 pages.

Gennisson et al., "Acoustoelasticity in Soft Solids: Assessment of the Nonlinear Shear Modulus with the Acoustic Radiation Force", J Acoust Soc Am (122), Dec. 2007, pp. 3211-3219.

Latorre-Ossa et al., "Quantitative Imaging on Nonlinear Shear Modulus by Combining Static Elastography and Shear Wave Elastography", IEEE Trans Ultrason Ferroelectr Freq Control, Apr. 2012; 59(4):833-9.

Mellema et al., "Probe Oscillation Shear Elastography (PROSE): A High Frame-Rate Method for Two-Dimensional Ultrasound Shear Wave Elastograpy", HHS Public Access Author Manuscript, Sep. 1, 2017, 22 pages.

O'Donnell et al., "Internal Displacement and Stain Imaging Using Speckle Tracking", IEEE Transactions o Ultrasonic, Ferroelectrics, and Frequency Control, vol. 41, Issue 3, May 1994, pp. 314-325.

Ophir et al., "Elastography: A Quantitative Method for Imaging the Elasticity of Biological Tissues", Ultrasonic Imaging, 1991, vol. 13, pp. 111-134.

PCT International Preliminary Reort on Patentability in International Application PCT/EP2020/085606, mailed Jun. 23, 2022, 16 pages.

PCT International Search Report and Written Opinion in International Application PCT/EP2020/085606, mailed Jun. 8, 2021, 27 pages.

Chinese Office Action dated Sep. 2, 2024, in Chinese Patent Application No. 202080082912.1 (with attached English Translation).

* cited by examiner

ULTRASONIC METHOD FOR QUANTIFYING THE NONLINEAR SHEAR WAVE ELASTICITY OF A MEDIUM, AND DEVICE FOR IMPLEMENTING THIS METHOD

This application is a National Stage Application of PCT/EP2020/085606, filed 10 Dec. 2020, which claims benefit of French Patent Application Serial No. FR1914432, filed 13 Dec. -2019, and which applications are incorporated herein by reference. To the extent appropriate, a claim of priority is made to each of the above disclosed applications.

TECHNICAL FIELD

This invention relates to ultrasonic wave imaging methods and devices for providing images of a viscoelastic medium. In particular, the method aims to quantify the nonlinearity of the medium, specifically to detect a soft cancerous region in the medium (i.e., non-indurated compared to non-cancerous medium).

More particularly, this invention relates to an imaging method using ultrasonic waves for observing scattering in a viscoelastic medium that contains reflective particles of said ultrasonic waves.

PRIOR ART

Ultrasound images may be obtained by different methods. For example, the images obtained can be of static strain type, obtained by deforming the observed tissue, or of shear wave elastography (SWE) type.

Indurated cancers are commonly detected by shear wave elastography (SWE) ultrasound imaging. However, this technique does not detect soft cancers given that such cancers have similar elasticity to non-cancerous media using conventional elastography.

Moreover, it is known to determine nonlinear properties of a medium, cf. for example:
H. Latorre-Ossa, J L Gennisson, E. De Brosses, M Fink, Quantitative imaging of nonlinear shear modulus by combining static elastography and shear wave elastography, IEEE Trans Ultrason Ferroelectr Freq Control. 2012 April; 59 (4):833-9, and
M. Bernal, F. Chamming's, M Couade, J Berfcoff, M. Tanterm J L Gennisson, In Vivo Quantification of the Nonlinear Shear Modulus in Breast Lesions: Feasibility Study. IEEE Trans Ultrason Ferroelectr Freq Control. 2016 January; 63 (1):101-9. doi: 10.1109/TUFFC.2015.2503601. Epub 2015 Nov. 24.

However, to retrieve information from the nonlinearity, several problems must be solved, in particular finding a mathematical expression that represents the nonlinearity of the shear modulus as a function of the shear modulus and the deformation, determining/measuring values that are necessary to calculate this mathematical expression, and establishing a measurement and calculation process that enables the retrieval of this data.

INVENTION DISCLOSURE

This invention therefore aims to improve detection and diagnosis of non-indurated cancer.

To this end, this invention provides a method for quantifying the nonlinear shear wave elasticity of a medium, using the following steps:

A1. Collecting a temporal succession of shear wave elasticity data from the medium,
A2. Applying a successively changing sequence of deformations to the medium according to a predetermined sequence during the collection of shear waves,
A3. Observing the actual (estimated) evolution of deformation, and
B. Quantifying the nonlinear elasticity of the medium as a function of temporal succession of data and evolution of deformation.

With these provisions, detection or diagnosis of soft cancers, e.g., breast cancer, by ultrasound image can be improved. Soft cancers show similar elasticity to healthy tissue or soft benign lesions on a standard SWE elastography image (without compression). However, it has been found that by compressing the tissue (medium) during SWE, the elasticity varies differently in healthy tissue and in malignant lesions. NL-SWE imaging aims to qualify and quantify this phenomenon.

For example, based on the theory of acoustoelasticity, the nonlinear shear modulus of tissue or the nonlinear elastic shear coefficient or stiffening can be deduced from strain and SWE images. Specifically, in this mode, by compressing or decompressing the tissue with the probe, the human operator (or machine, or anything that can handle or operate an ultrasound probe), can acquire a series of SWE and strain images used to deduce a map that represents the nonlinearity of the shear modulus or stiffening rate of the medium.

Furthermore, this invention may solve the following problems in particular, with the aim of retrieving data from the nonlinearity:

1. Find a mathematical expression that represents the nonlinear shear modulus as a function of shear modulus and deformation.
2. Develop an ultrasound sequence that can simultaneously acquire B-mode images, shear wave elastography (SWE) images and strain elastograms (by deformation).
3. Develop a technique to aggregate and re-align strain and SWE images during compression; or at the end of compression or at dedicated steps during the compression process.
4. Develop a user interface that guides the operator in performing compression/decompression.
5. Create a probe attachment that guides compression/decompression.

In different embodiments of the method according to this invention, one and/or another of the following provisions may optionally be further employed.

According to one aspect, observing the evolution of real deformation occurs in real or near real time. Thus, thanks to this real-time or near-real-time observation, deformation can be carried out continuously and progressively (i.e., without pausing).

According to one aspect, successively changing deformation is applied via an ultrasonic probe by successively compressing or successively decompressing the medium through the probe, the probe being simultaneously used to collect the temporal succession of data and/or to observe the evolution of real deformation. This method may employ a motion estimation algorithm, including (but not limited to), a method based on the Doppler effect, speckle tracking, and/or optical flows.

Observation of the evolution of real deformation can be represented or measured by the medium strain (as described below).

According to one aspect, successive compression and/or decompression is performed continuously and progressively. For example, compression and/or decompression is a continuous movement without pausing or stopping.

According to one aspect, the step consisting in observing the evolution of real deformation comprises collecting a temporal succession of ultrasound data of the medium, in particular to make deformation calculations possible, for example collecting a temporal succession of static elasticity (strain) data.

According to one aspect, an estimated real deformation level and a target deformation level are reported on a user interface, wherein the estimated real deformation corresponds to the observed deformation, particularly in real time, and the target deformation changes (particularly continuously and progressively) according to the predetermined sequence of deformations, particularly in real time.

It is noted that the real deformation level may only be estimated, i.e., this level may be somewhat imprecise.

According to one aspect, the estimated real deformation level and the target deformation level are displayed on a user interface screen.

According to one aspect, the shear wave elasticity data produced in Step (A1) is generated by the following sub-steps:

A1.1. an excitation step during which a shear wave is generated in the medium, by emitting at least one focused ultrasound wave, A1.2. an observation step during which the shear wave propagation is observed by acquiring a temporal succession of ultrasound data of the medium, A1.3. a processing step in which elasticity data is determined from said medium ultrasound data and a shear wave propagation model.

This process can use plane waves but this step can also be performed using focused waves.

According to one aspect, temporal data collection and observation of successive changes in deformation are achieved using an ultrasound sequence with interleaved shear wave elasticity bursts and static elasticity bursts, and/or said static elasticity data and said shear wave elasticity data are temporally interleaved.

The process may further include Step: A1'. Collecting a temporal succession of data on the static elasticity ($\Delta\varepsilon_t$) of the medium.

In Step A3, the actual deformation can be deduced by the static elasticity ($\Delta\varepsilon_t$).

This static elasticity can be a Lagrangian static elasticity ($\Delta\varepsilon_t$).

In particular, the temporal succession of data on the static elasticity ($\Delta\varepsilon_t$) may comprise a temporal succession of static elasticity values ($\Delta\varepsilon_t$). The temporal succession of shear wave elasticity data (Et) comprises a temporal succession of shear wave elasticity values (Et), Total static elasticity ($\varepsilon_t$) can be determined as a function of integration of the static elasticity values ($\Delta\varepsilon_t$).

In Step A3, the actual deformation can be determined as a function of the determined total static elasticity ($\varepsilon_t$).

The process may further include Step: A6'. Determining a quality parameter based on at least one of the following parameters: shear wave elasticity (Et), static elasticity ($\Delta\varepsilon_t$) and total static elasticity ($\varepsilon_t$).

The quality parameter can be determined as a function of comparing a current value ($\varepsilon_t$) and a previous value ($\varepsilon^*_{t-1}$) of the total static elasticity.

The quality result can be a Boolean variable.

The quality parameter can be determined as a function of whether the current value ($\varepsilon_t$) exceeds the previous value ($\varepsilon^*_{t-1}$) of the total static elasticity increased or decreased by a first difference threshold. This predefined difference threshold can be fixed or according to a predefined function.

The quality parameter can be determined as a function of a minimum period of time, during which the estimated real deformation level (shown by the total static elasticity ($\varepsilon_t$)) corresponds to the target deformation level (e.g., with a predefined tolerance).

The quality parameter can be determined as a function of whether an entropy of the current values of the shear wave elasticity (Et), and/or the static elasticity ($\Delta\varepsilon_t$) lie within a predefined range.

As long as the determined quality parameter exceeds a first minimum quality threshold, in Step B, the current values of the shear wave elasticity (Et*), and the total static elasticity ($\varepsilon^*_t$) can be used to quantify the nonlinear elasticity of the medium. Hence, only values of an acceptable quality level can be used. However, non-qualified values can be used as comparison values in the next t+1 cycle.

As long as the determined quality parameter does not exceed the minimum quality threshold, optional actions are available:
- current shear wave elasticity (Et), and total static elasticity ($\varepsilon_t$) values are not used to quantify the nonlinear elasticity of the medium, and/or
- feedback information reflecting the determined quality parameter is provided to the probe user, and/or
- the process is optionally repeated in a next cycle (t+1).

The predetermined sequence of deformations may be adapted as a function of the quality parameter.

The predetermined sequence of deformations may be interrupted or paused if the determined quality parameter does not exceed the minimum quality threshold.

Thus, the predetermined sequence of deformations may be predefined but may also optionally depend on the quality of the acquired data.

The method may further comprise Step: C. Determining visual information that shows the level of nonlinear elasticity of the medium comprising at least one of the following: an image, a score, and/or a symbol showing the level of nonlinear elasticity of the medium.

The method may further comprise Step: D. Presenting feedback information to a probe user, including at least one of the following: the real deformation, the quality parameter, and the visual information.

Steps A1. to B. or A1. to C. or A1. to D. may be repeated, and/or Steps A1. to B. or A1. to C. or A1. to D. may be repeated until one of the following conditions is met: the determined quality parameter does not exceed a second minimum quality threshold which is lower than the first minimum quality threshold, and/or a maximum number of iterations has been performed, and/or a maximum process time has elapsed, and/or a minimum number of quantifications of the nonlinear elasticity of the medium has been performed.

The process may therefore comprise several t cycles, during which the determined values are updated and/or refined.

According to one aspect, the method may further comprise Step C. of determining an image and/or a score and/or a symbol showing the level of nonlinear elasticity of the medium.

The score and/or symbol may be an icon, a value versus a threshold, phrases, a table of values, etc.

According to one aspect, the method may further comprise the following Steps:
A4. Gathering a temporal succession of B-mode data from the medium to calculate a motion compensation of the medium relative to the probe,
A5. Applying the compensation to the elasticity data.

According to one aspect, the B-mode data, the static elasticity data and the shear wave elasticity data are temporally interleaved.

According to one aspect, Steps (A1) to (A3) or (A1) to (A5) or (A1) to (D) are performed simultaneously, and/or Steps (A1) to (A3) or (A1) to (A5) or (A1) to (D) are performed in real time or near real time.

According to one aspect, for each moment of the temporal succession of data or at least for some of the moments, the value of a nonlinearity parameter of the shear waves is determined by performing a linear regression fit according to the following equation:

$$\log(E(t)) = \log(E_0) - \varepsilon \frac{3A}{4E_0} \qquad \text{[Math. 1]}$$

where:
E(t) is the elasticity at each moment of deformation during the evolution of deformation,
$E_0$ is the elasticity at a first moment (t0),
ε is the deformation, and
A is the shear nonlinearity parameter.

According to one aspect, the method further comprises a step (0) prior to Step (A1), where at least one ultrasound or MRI (magnetic resonance imaging) or mammography or shear wave elasticity image of the medium is determined, without the application of a deformation according to a predetermined deformation sequence, and this step makes it possible to determine a region of interest (ROI) for which the nonlinear elasticity is quantified according to Steps (A1) to (B).

According to one aspect, a confidence map comprising reliability levels is displayed alongside the nonlinear elasticity image, in order to allow the practitioner to know the evaluated confidence level of each point of the "result" image presented.

This confidence map can be a map (or an image) that indicates the reliability level of each part of the image showing the level of nonlinear elasticity of the medium. The reliability level may be deduced, for example, from statistics derived from the result of the linear regression and/or may take into account the characteristics of the actual motion applied to the tissue (uniform velocity, uniaxial motion, . . . ). This map may be implemented using matrices, images, color codes, and/or tables.

According to one aspect, a nonlinear elasticity value with respect to a predefined reference value is displayed for each data or for each pixel of the image. This predefined reference value can be a predefined value from the scientific literature and/or can be calculated for this same patient during a previous examination, or be the result of statistical calculations and may optionally be displayed graphically. For example, the value may be displayed instead of or in addition to the nonlinear elasticity value (e.g., for each pixel or group of pixels). Display of the predefined value can beneficially allow for reliable analysis and/or diagnosis of, for example, a soft cancerous medium and/or indicate the type of cancer observed.

This invention also relates to an ultrasonic method for quantifying the nonlinear shear wave elasticity of a medium using an imaging device (1) comprising an ultrasonic probe (6), a microcomputer (4), and optionally a user interface, the method comprising the following steps:
positioning the probe on the surface of the medium,
activating a first nonlinear shear wave elasticity (NL-SWE) imaging mode, during which, with the probe applying a deformation according to a predetermined sequence of deformations, progressively compressing or progressively decompressing the medium:
the device gathers a temporal succession of ultrasonic data imaging the shear waves generated in the medium using the probe to infer the elasticity of the medium, and
the device gathers a temporal succession of ultrasound data making it possible to deduce the evolution of deformation of the medium applied by the probe,
quantifying the nonlinear elasticity of the medium, which is calculated as a function of the temporal succession of data and the observed evolution of deformation,
optionally displaying an image of the nonlinear elasticity of the medium on the user interface,
optionally saving the temporal succession of images, including predefined image calculations and measurements,
optionally displaying the temporal succession of images on the user interface,
optionally displaying an interpretation result of the nonlinear image.

Each of these images can be two-dimensional or 3D.

Before launching this NL-SWE mode, a step consisting in setting the parameters of the pre-determined sequence of deformations, e.g., according to the clinical case (patient's size, size of the organ considered, in particular when it concerns breast tissues, depth of the lesion observed, density of the tissues, etc.) can be carried out.

In addition, once the nonlinearity image is displayed, a step consisting in setting the display parameters, e.g., according to user preferences (overlay with other B-mode images, etc.), changing the units, changing the color code, etc.

As compression (stress) or decompression is a progressive movement, a user or an articulated arm or any other operator can perform it continuously, without pausing.

During each of the collection steps of the process, the probe can collect ultrasound data on which a motion estimation method (speckle tracking on B-mode or Doppler effect) can be applied in order to extract information related to the deformation and/or in order to realign the collected ultrasound data.

According to one aspect, the predetermined sequence of deformations comprises an optionally automatic stop sub-step before the quantization step. This provides the added benefit for the operator of being notified, for example, that the acquisition session is over because sufficient data has been collected.

According to one aspect, the method may further comprise, particularly before activating the first mode:
positioning the probe on the surface of the medium,
activating a second shear wave elasticity (SWE) imaging mode, determining at least one shear wave elasticity image of the medium by applying shear waves in the medium without applying a deformation according to a predetermined sequence of deformations, saving the image, optionally including predefined image calculations and measurements determining an area of interest in the image to image the nonlinear elasticity of the area.

Furthermore, this invention provides a method for determining a non-indurated cancerous medium in comparison to the non-cancerous medium (a non-indurated malignant lesion in comparison to a benign lesion) using the method as set forth above, wherein the non-indurated cancerous medium (non-indurated malignant lesion) is detected according to its level of nonlinear elasticity.

Specifically, this invention provides a method for determining a non-indurated cancerous medium in comparison to non-cancerous medium using the method as set forth above, wherein the medium examined is biological breast and/or axillary tissue.

This disclosure also relates to an imaging device comprising an ultrasound probe and a microcomputer adapted to implement the method for quantifying the nonlinear elasticity of a medium as set forth above.

DESCRIPTION OF EMBODIMENTS

Across the various figures, provided for illustrative purposes, the same numerical references denote the same or similar elements.

Figure 1:
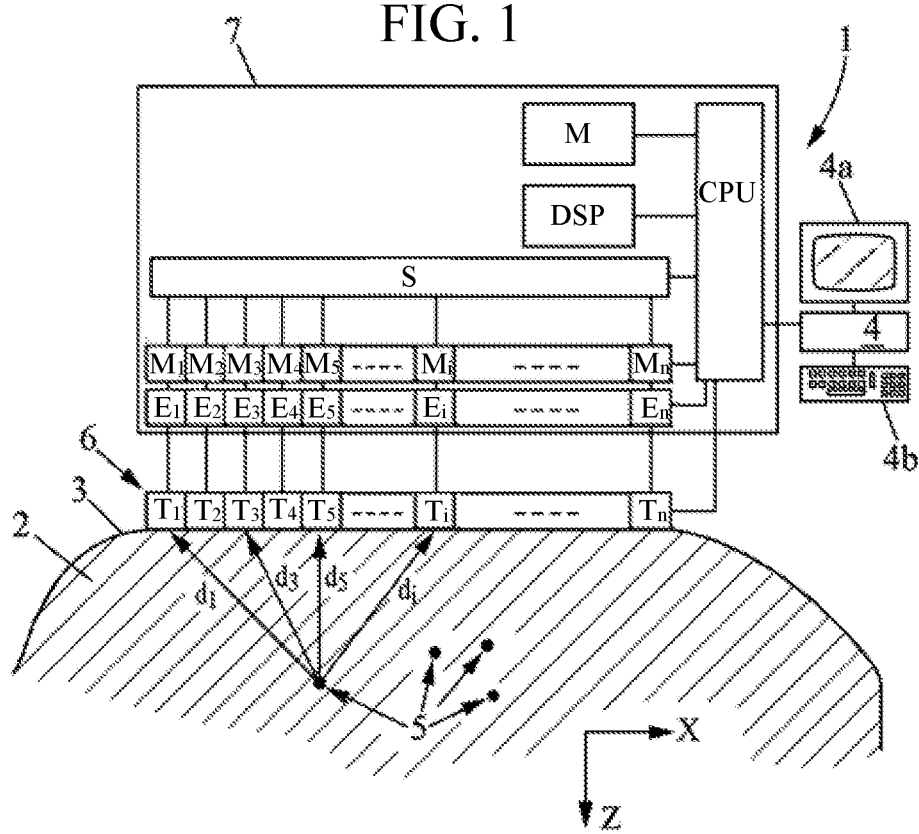
FIG. 1 is a schematic view of an ultrasound imaging device according to one embodiment of the invention.

Imaging device 1 shown in FIG. 1 is intended to provide images of a viscoelastic medium 2 which scatters ultrasound compression waves, and which may be for example a living body, e.g., a part of the body of a patient (breast, liver, abdomen, etc.), in the case of medical applications. Imaging device 1 is also able to examine elastic shear wave propagation to provide elasticity images of the medium 2.

Images of the medium are produced, for example, by means of a microcomputer 4 (comprising at least one input interface 4b such as a keyboard or similar, and an output interface 4a such as a screen or similar) or any other electronic central unit, which sends ultrasound compression waves into the medium 2 from its outer surface 3, which interact with the scattering particles 5 contained in the medium 2, these particles being reflective for the ultrasound compression waves. The particles 5 may be constituted by any heterogeneity of the medium 2, and in particular, for medical applications, by collagen particles present in human tissues (these particles form so-called "speckles" on the ultrasound images).

To observe the medium 2 and generate images of the medium, an ultrasonic probe 6 is placed against the outer surface 3 of the observed medium 2. This probe sends compression ultrasonic wave pulses along a Z axis, such as those commonly used in echography, at a frequency of, for example, between 0.5 and 100 MHz and preferably between 0.5 and 15 MHz, e.g., of about 4 MHz.

The ultrasonic probe 6 consists of an array of n ultrasonic transducers T1, T2, . . . , Ti, . . . , Tn, n being an integer greater than or at least equal to 1.

This probe 6 may take the form, for example, of a linear array that may comprise, for example, n=128 transducers aligned along an X axis perpendicular to the Z axis. The probe in question may also be a two-dimensional array (plane or not) of transducers.

Transducers T1, T2, . . . Tn can be controlled independently of each other by the microcomputer 4, possibly via a central processing unit (CPU) which is contained, for example, in an electronic rack 7 connected to the probe 6 by a flexible cable.

Transducers T1-Tn can thus selectively emit:

either a plane ultrasound compression wave (i.e., in this case a wave whose wavefront is rectilinear in the X, Z plane) or any other type of unfocused wave illuminating the entire field of view in the medium 2, for example a wave generated by having the various transducers T1-Tn emit random acoustic signals, or an ultrasound compression wave focused on one or more points in the medium 2.

US 2009/234230 proposes a synthetic imaging technique that uses multiple unfocused compression waves, e.g., plane waves of different angles, and combines the returning waves of these plane waves to very quickly obtain an image of the medium with improved quality.

The imaging device 1 and method according to this invention perform shear wave nonlinear elasticity quantification of a medium. To initiate this process, a first imaging mode of nonlinear shear wave elasticity (NL-SWE) can be activated.

The NL-SWE mode uses an ultrasonic method to determine the shear wave elasticity (SWE) of the medium.

This process (i.e., the respective data collection or scan) may be combined simultaneously and/or interleaved with an ultrasonic process to observe the evolution of deformation in real time or in near real time.

Detailed examples of these three ultrasonic processes are explained in detail below. SWE and strain processes may be based on plane ultrasound waves, whereas the B-mode process may be based on non-plane ultrasound waves.

As an alternative to or in addition to the ultrasonic method for determining static elasticity (strain), the probe may also be equipped with a pressure sensor to observe (or follow) the evolution of deformation in the medium.

Figure 2A:
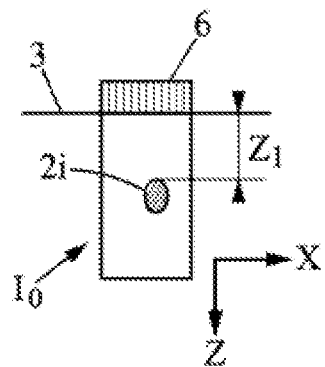
FIGS. 2A, 2B and 2C schematically illustrate an example of the process according to this invention, in particular the application of a successively changing schematic deformation to the medium.
Figure 2B:
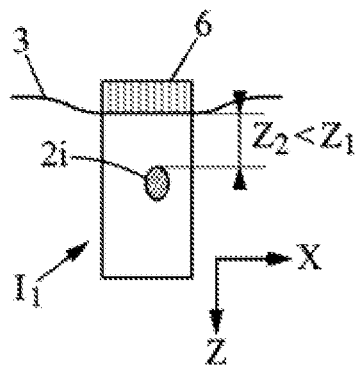
Figure 2C:
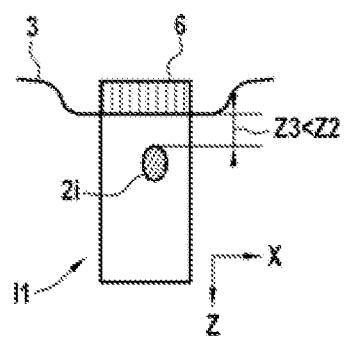

FIGS. 2A to 2C provide an example of the process according to this invention, in particular applying a successively changing schematic deformation to the medium.

In this example, the process begins in the state illustrated in FIG. 2A and ends in the state illustrated in FIG. 2C. FIGS. 2A to 2C show in particular the evolution of deformation of the medium caused by applying a successively changing deformation to the medium. The imaging device 1 simultaneously performs shear wave nonlinear elasticity quantification of the medium according to this invention.

The process may take a few seconds, e.g., between 5-10 s. This time is useful to collect enough data during the evolution of deformation of the medium (i.e., to sufficiently quantify the nonlinear shear wave elasticity of a medium during this evolution).

The user may be alerted via a countdown so that he/she is ready to apply the deformation to the tissue through the probe or any other means.

The deformation illustrated in FIGS. 2A to 2C is only schematic. The deformation level that is applied according to this disclosure is predetermined by a predefined sequence of deformations, as explained in the context of FIGS. 3A to 3C.

FIG. 2A depicts operation of the imaging device 1 at time t0 of the process, with the probe 6 exerting little or no external pressure P on the external surface 3. The external surface 3 remains substantially horizontal (in the X direction). The image of medium $I_0$ includes, for example, an inclusion 2i at a depth Z1 relative to the external surface 3. Concurrently, the ultrasonic process for quantifying the nonlinear shear wave elasticity of the medium (as explained above) is started.

FIG. 2B depicts operation of the imaging device 1 at time t1 of the process, and with an external pressure P' (or stress) exerted, greater than P, which deforms the outer surface 3 in the Z direction toward the interior of the medium 2. Thus, the medium deformation has been successively changed.

FIG. 2C depicts operation of the imaging device 1 at time t2 of the process, with an external pressure P''' even higher than P' exerted at t1.

Successive compression, as shown in FIGS. 2A to 2C, can be carried out in a continuous and progressive manner. This is possible thanks to observation of the evolution of real deformation in real time or in near real time. Alternatively, successive decompression can be applied to the tissues comprising the medium.

As already indicated, the evolution of deformation shown in FIGS. 2A to 2C is not random, but is predetermined by a predefined sequence of deformations. For example, this sequence may, for instance, be graphically illustrated to the user on a user interface screen 4a of the device 1, thus allowing the user to apply the correct pressure at each moment of the process. For instance, a cursor display indicating the pressure to be applied as well as the applied pressure measured on the same graph or vibrations in the probe to indicate to the user if he or she is following the predefined sequence. It is also possible to automate the deformation process, such as by using a robotic arm that moves the probe in an automated way according to the predefined sequence.

Figure 3A:
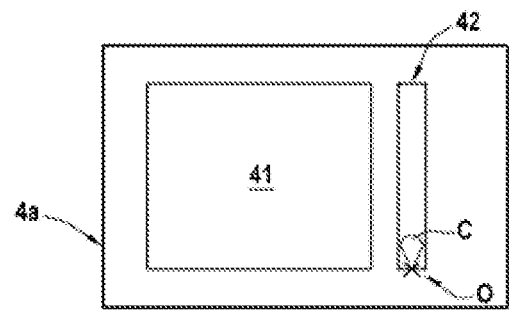
FIGS. 3A, 3B, and 3C are schematic illustrations of a device user interface screen when performing a method according to this disclosure.
Figure 3B:
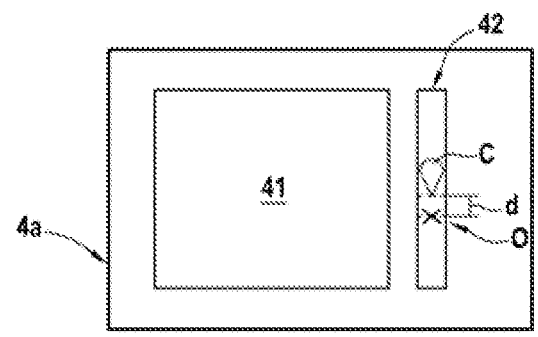
Figure 3C:
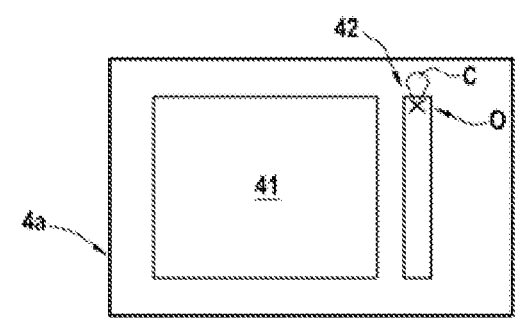

FIGS. 3A to 3C show an example screen 4a of a device user interface during a process according to this disclosure. For example, FIGS. 3A to 3C may refer to the time moments t0-t2 in FIGS. 2A to 2C.

Screen 4a may display a field 41 to show at least one ultrasound image. For example, this image may be an image of an area of interest in the medium (e.g., a shear wave elasticity (SWE) image) that was taken prior to starting the process, i.e., before t0. After moment t2, field 41 can display an image showing the nonlinear elasticity level of the medium according to this invention.

Screen 4a further shows field 42. During the process, said field 42 displays the current estimated real deformation level (e.g., with a cross or point O) and the target deformation level (e.g., with a ball or circle C).

The estimated real deformation O is the currently observed deformation, particularly in real time, and the target deformation C changes successively according to the predetermined sequence of deformations, particularly in real time. Target C may evolve successively in field 42 during the process, in order to show the evolution of the predetermined sequence of deformations at each moment and thus, guide the user.

FIG. 3A may reflect the state of FIG. 2A and thus time instant t0. As a result, the probe 6 exerts little or no external pressure O on the external surface 3. Thus, the current estimated real deformation level O and the current target deformation level C are both zero.

FIG. 3B may reflect the state of FIG. 2B and thus time moment t1. Hence, the probe 6 exerts an increased external pressure P on the external surface 3. In this example scenario, there is a level difference between the estimated real deformation O and the current target deformation level C. In this example, the current estimated real deformation level O is lower than the current target deformation level C. That is, the user is guided by the target C to increase the pressure further.

FIG. 3C may reflect the state of FIG. 2C and thus time moment t2. Hence, the probe 6 exerts an even higher external pressure P''' than P' at t1. Since t2 is the end of the predetermined sequence of deformations, the current estimated real deformation level O and the current target deformation level C are both at the maximum of the predetermined sequence of deformations.

Optionally, the imaging is stopped or frozen at time moment t2. This allows the user beneficially to focus on the predefined sequence of deformations until t2, without having to stop the imaging manually.

At time moment t2 or after, or during data acquisition, device 1 quantifies the nonlinear elasticity of the medium, which is calculated as a function of the temporal succession of data and the observed evolution of deformation during time t0 to t2. The user interface may display an image of the nonlinear elasticity of the medium on field 41, which is determined as a function of the quantized nonlinear elasticity. Optionally, the device 1 may record the temporal succession of data (or images) collected during time t0 to t2. This step can include predefined data calculations and measurements. In addition, the screen 4a may display the temporal succession of images on the user interface.

Once the image has been displayed, the user can set the display parameters according to his or her preferences (overlay with other images, B-mode, etc.), change the units, change the color code. For example, it is possible to switch between a display without units, which is easier to interpret, and a display with units (e.g., kPa), which may be beneficial for use with scientific literature to interpret the values. These analyses may be performed through statistical algorithms by any means, e.g., artificial intelligence.

In addition, the device may involve a second mode of ultrasound imaging, and/or shear wave elasticity (SWE) imaging, and/or mammography. This mode can be activated before using the NL-SWE mode or during a previous stand-alone session. In this mode, the device can determine at least one shear wave elasticity image of the medium by applying shear waves in the medium, without applying a deformation according to a predetermined sequence of deformations. The image can be saved, optionally including predefined image calculations and measurements. The user can then determine a region of interest (ROI) in the image to image the nonlinear elasticity of the region according to the first NL-SWE mode.

Figure 4:
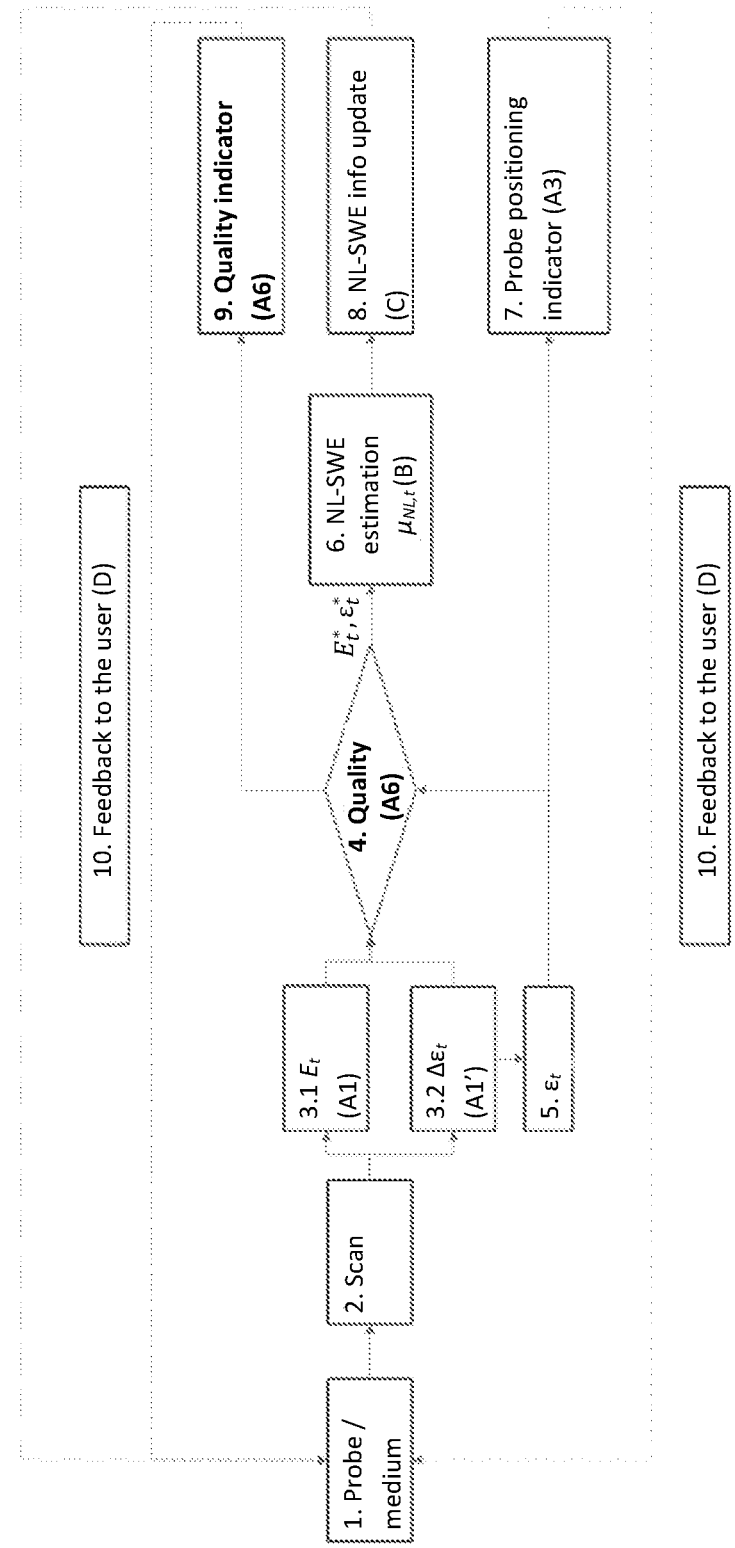
FIG. 4 schematically illustrates a logigram of an improved process according to this disclosure.

FIG. 4 is a schematic illustration of a flowchart of an improved process according to this disclosure. This process includes in particular a quality criterion for the collected data.

The process can be repeated for multiple cycles t. Thus, the process may last for a variable period of time including the multiple cycles t. This variable time or duration and/or number of cycles may be predefined and adapted according to the quality of the acquired data (as described below). The process can be repeated until one of the following conditions is met: The determined quality parameter does not exceed a second minimum quality threshold that is lower than the first minimum quality threshold, and/or a maximum number of iterations has been performed, and/or a minimum number of quantification of the nonlinear elasticity of the medium has been performed.

In Step 1, the user positions the probe on the surface of the medium. In Step 2, a scanning or imaging mode is activated. This mode includes in particular shear wave elasticity (SWE) imaging and static elasticity (strain) imaging, during which the probe applies a deformation according to a predetermined sequence of deformations, gradually compressing or gradually decompressing the medium. The Step 2 scan can last for the variable time of the process.

In Step 3.1, a temporal succession of ultrasound data imaging the shear waves generated in the medium is collected with the probe, making it possible to deduce the shear wave elasticity (SWE) $E_t$. This step may be Step A1 according to the disclosure. In particular, for each cycle t during the scan in Step 2 Young's modulus $E_t$ of actual shear wave velocity measurement can be collected.

In Step 3.2, a temporal succession of static elasticity data of the medium is collected using the probe to deduce the static elasticity $\Delta\varepsilon_t$ of the medium. This step may be Step A1' according to the disclosure. In particular, for each cycle t during the scan in Step 2 the instantaneous static (Lagrangian) elasticity $\Delta\varepsilon_t$ is deduced by comparing the current and historical images. For example, the static elasticity is determined by comparing the current (t) and previous (t−1) RF echo values of the received radio-frequency echoes from the medium.

The temporal succession of static elasticity data $\Delta\varepsilon_t$ may comprise a temporal succession of static elasticity values (in particular one value per cycle t), and/or the temporal succession of shear wave elasticity data (Et) comprises a temporal succession of shear wave elasticity values (in particular one value per cycle t).

In Step 5, the total static (axial) elasticity is calculated $\varepsilon_t$ by integrating the static elasticity $\Delta\varepsilon_t$. This total static elasticity $\varepsilon_t$ is sent to the qualifier (see Step 4). This total static elasticity $\varepsilon_t$ is also used to determine the real deformation and/or to update the probe position indicator in Step 7 (i.e., the current estimated real deformation level O in FIGS. 3A to 3C). These Steps 5 and/or 7 may be Step A3 according to the disclosure.

In Step 4, the quality of the collected data is quantified. In particular, a quality parameter is determined. The predetermined sequence of deformations can be adapted according to the quality parameter, and/or the predetermined sequence of deformations can be interrupted or paused, if the determined quality parameter does not exceed the minimum quality threshold (i.e., a first quality threshold). For example, in case the determined quality parameter does not exceed the minimum quality threshold, the current values are not used and the quality is measured again in a next cycle t+1 based on future values of shear wave elasticity $E_{t+1}$, static elasticity $\Delta\varepsilon_{t+1}$ and total static elasticity $\varepsilon_{t+1}$.

Should the determined quality parameter exceed the first minimum quality threshold in Step 4, the current values of the shear wave elasticity and the total static elasticity are reported as qualified Et* and $\varepsilon^*_t$ values and these values are used to quantify the nonlinear elasticity of the medium. A non-exhaustive description of the possible determinations of the quality parameter is given below in Options 1 to 3.

In Step 9, the quality and/or the quality parameter may be presented as an image, a score, and/or a symbol showing the quality level. In particular, the quality result may be presented as a Boolean value (e.g., a traffic light with red or green colors, and optionally with other colors for detail, e.g., amber, and/or a smiley face), as a numerical indicator on a scale (e.g., from 0 to 10), and/or as an indication of a movement to be made with the probe (e.g., an arrow with a length and/or width adapted according to the quality parameter).

Consequently, feedback information may be presented to the user depending on the quality parameter (see Step 10). For example, in case the quality of the acquired data is not acceptable (e.g. the quality parameter does not exceed a predefined quality threshold) the user is informed to continue the scan and the future data (t+1) will be tested again. These Steps 4 and/or 9 may be Step A6 according to the disclosure.

In Step 6, qualified values of the total static elasticity $\varepsilon^*_t$ and shear wave elasticity (SWE) $E^*_t$ are used to calculate the nonlinear shear wave elasticity $\mu_{NL,t}$ (NL-SWE).

In Step 8, the $\mu_{NL,t}$ value is used to update the nonlinear shear wave elasticity (NL-SWE) information, e.g., a SWE-NL map. This information may also be presented for example as an image, a score, and/or a symbol showing the level of nonlinear elasticity of the medium. The update may be performed in real time or near real time during the scan for each cycle t. In particular, the NL-SWE map may be refined with each $\mu_{NL,t}$ value, i.e., in each cycle t. Step 8 may be Step C according to the disclosure.

In Step 10, feedback information is presented to the probe user, in real time or in near real time, during the scan for each cycle t. This information may include the real deformation updated in Step 7, the quality parameter updated in Step 4, and/or the nonlinear shear wave elasticity (NL-SWE) information updated in Step 8. Step 10 may be Step D according to the disclosure.

A non-exhaustive description of the possible determinations of the quality parameter is given below. These determinations may be used individually or in combination.

Option 1: Qualification by Static Elasticity

The quality parameter can be determined as a function of comparing a current $\varepsilon_t$ value and a previous $\varepsilon^*_{t-1}$ value of the total static elasticity. In particular, the quality parameter can be determined as a function of whether the current $\varepsilon_t$ value exceeds the previous $\varepsilon^*_{t-1}$ value of the total static elasticity increased by a first difference threshold. In this case, the current values of the shear wave elasticity and the total static elasticity are reported as qualified Et* and $\varepsilon^*_t$ values and are used to quantify the nonlinear elasticity of the medium. Target C (see FIG. 3A-C) may move to an increased deformation level.

This predefined threshold may be set at time t or may be calculated (e.g., in real time) according to a predefined function.

Optionally, if the previous $\varepsilon^*_{t-1}$ value exceeds the current $\varepsilon_t$ value, e.g., increased by a second difference threshold (i.e., a second quality threshold lower than the first quality threshold is not reached), the process for quantifying the nonlinear elasticity (e.g., the scan) may be stopped and optionally an error and/or a message that the process be terminated may be indicated to the user.

The description above assumes that the user applies successive compression during the scan. However, it is also possible that the user applies successive decompression during the scan. In other words, before the start of the scan, the user applies a compression according to a first compression level and then decompresses during the scan. In this scenario, the process of comparing a current $\varepsilon_t$ value with a previous $\varepsilon^*_{t-1}$ value, using a threshold, is reversed in correspondence. The scan may be stopped when a second predefined compression level (lower than the first compression level) is reached. Optionally a message indicating that the process is finished may be indicated/presented to the user. The first compression level may be user-selected (i.e. defined by the maximum pressure level applied) and/or may be predefined by the process (e.g. by indicating a target pressure level). The second compression level may be set or may be chosen according to a predefined function, e.g. depending on the first pressure level, and/or depending on whether enough data is collected to quantify the nonlinear elasticity.

Option 2: Qualification by Workflow

The quality parameter may also be determined as a function of a predefined period of time, where the estimated real deformation level represented by the total static elasticity $\varepsilon_t$ equals the target deformation level, in particular with a predefined tolerance. Thus, if the probe location matches the target location C (see FIG. 3A to C) during the time period (i.e., a first quality threshold is reached), the current values of shear wave elasticity and the total static elasticity are reported as qualified Et*, values and are used to quantify the nonlinear elasticity of the medium. This result may be indicated to the user in Step 10, for example by displaying a certain color on the quality indicator. Target C may move to an increased deformation level.

However, if the probe does not reach the target location, the target may remain at its level. If the probe does not reach the target location for a period of time that is longer than the predefined duration (i.e., a second quality threshold lower than the first quality threshold is not reached), the process for quantifying the nonlinear elasticity (and/or the scan) may be stopped and optionally an error and/or a message specifying that the process has ended may be indicated to the user.

The predefined duration may comprise at least one cycle t and is advantageously shorter than the varying process time. For example, the predefined duration may be less than one second (e.g., 30 ms to 100 ms) and the variable process time may last several seconds. If the predefined time consists of several cycles t, it is possible that during the cycles only Steps 1 to 4 are performed and Steps 6 to 10 are performed only afterwards. The predefined time may be fixed or may be adapted according to a predefined function.

Furthermore, the variable time for the process to quantify the nonlinear elasticity (and/or the scan) may stop automatically after a maximum limit.

In this context it should be noted that keeping track of the scan time is beneficial, as the medium can be heated by the waves. It is therefore desirable to stop the process after the maximum time and/or to finalize the data acquisition quickly.

The Option 2 scenario also allows the user to freely apply compressions and/or decompressions during the scan. In this case the predetermined sequence of deformations may be realized as one or more compression levels. For example, the method may provide a minimum and a maximum threshold level.

Option 3: Qualification by Instantaneous Measurement

The quality parameter can also be determined if an entropy of the current values lies within a predefined range (i.e., if this entropy is bounded within a predefined interval, and/or if a first threshold is reached), in particular of the current values of the shear wave elasticity (Et), and/or the static elasticity ($\Delta\varepsilon_t$).

In this case, the current values of the shear wave elasticity and the total static elasticity are reported as qualified Et* and $\varepsilon^*_t$ values and used to quantify the nonlinear elasticity of the medium. This result may be indicated to the user in Step 10, for example by displaying a certain color on the quality indicator. Target C may move to an increased deformation level.

The Option 3 test can have the precondition only if the previous $\varepsilon^*_{t-1}$ value does not exceed the current $\varepsilon_t$ value, e.g. increased by a second difference threshold (i.e. a second lower quality threshold of the first quality threshold is not reached). In this case, the process for quantifying the nonlinear elasticity (e.g. the scan) can be stopped and optionally an error and/or a message indicating that the process is finished can be notified to the user.

Determining Images of the $I_k$ Medium in "B-mode"

The process described below is known as "B-mode" imaging. B-mode temporal succession of data (or image or image data) may be used to calculate a motion compensation of the medium relative to the probe when applying a successively changing deformation (as described above).

To generate an image of the medium (I), the imaging device performs for example the following steps:
- (i1) the microcomputer 4 causes the probe 6 to emit at least one unfocused ultrasound compression wave burst into the viscoelastic medium,
- (i2) the microcomputer 4 causes the probe 6 to detect and record acoustic signals received from the viscoelastic medium 2 in real time, comprising the echoes generated by the unfocused ultrasound compression wave by interacting with the reflecting particles 5 of the viscoelastic medium, and
- (i3) a processing step in which the microcomputer 4 processes the acoustic signals received from the viscoelastic medium 2 in sub-step (i2) to determine one or more images of the medium (I).

The unfocused ultrasound compression wave propagates through the medium 2 with a very high propagation speed, e.g., about 1500 m/s in the human body, and interacts with the reflecting particles 5, generating echoes or similar signal disturbances, known as speckle noise in the field of ultrasound imaging.

The speckle noise is picked up by the T1, . . . , Tn transducers during sub-step (i2), after the unfocused ultrasound compression wave burst. The si(t) signal thus captured by each Ti transducer is first sampled at high frequency (e.g. 30 to 100 MHz) and digitized in real time by a sampler in the rack 7 and connected to this transducer, respectively E1, E2, . . . En.

The si(t) signal thus sampled and digitized is then stored, also in real time, in a Mi memory in the rack 7 and specific to the Ti transducer.

Each Mi memory has, for example, a 128 MB capacity, and contains all the si(t) signals received.

Once all the si(t) signals have been saved, the central processing unit (CPU) reprocesses these signals by means of a summing circuit S in the rack 7 (or it carries out this processing itself, or the said processing may be carried out in the microcomputer 4), by means of a standard path formation process as per sub-step (i3).

Signals S(x,z) are thus generated, these signals each corresponding to the field of view image of the medium following the unfocused ultrasound wave burst.

For example, an S(t) signal can be calculated using the following formula:

$$S(x, z, t) = \sum_{i=1}^{n} \alpha_i(x, z) \cdot si\left[t(x, z) + d_i(x, z)/V\right] \quad \text{[Math. 2]}$$

where:
- si is the raw signal perceived by transducer No. i following the ultrasound compression wave burst,
- t(x,z) is the time taken by the ultrasound compression wave to reach the point in the field of view with coordinates (x,z), with t=0 at the beginning of the burst,
- di(x,z) is the distance between the point in the field of view with coordinates (x,z) and transducer No. i, or an approximate value of this distance,
- V is the average propagation velocity of the ultrasound compression waves in the observed viscoelastic medium, and
- αi(x,z) is a weighting coefficient taking into account apodization laws (in practice, it may be considered in many cases that αi(x,z)=1).

The above formula applies mutatis mutandis when the field of view is 3-dimensional (two-dimensional array of transducers), replacing the spatial coordinates of the (x,z) plane by spatial coordinates (x,y,z).

Following the optional path formation step, the CPU stores the S(x,z) image signals corresponding to the last burst into a main memory M in rack 7. These signals can also be stored in the microcomputer 4 in order for it to calculate the image of the medium (I) itself.

Other techniques for generating images of the medium (I) exist, such as synthetic imaging techniques. Any imaging technique for obtaining images of the medium may be used. Ideally, a technique that can obtain images at high speed will be used.

Determining Static Elasticity (Strain)

The process described below is known as static elasticity (strain) imaging. The temporal succession of static elasticity (strain) data (or image or image data) can be used to observe the estimated evolution of real deformation (as described above).

The images of the medium ($I_k$) may be processed by correlation and beneficially by cross-correlation either two by two, i.e. between an image of the medium of index k ($I_k$) and the image of the medium of index k−1 ($I_{k-1}$).

Cross-correlation may be performed, for example, in a specialized electronic circuit DSP in the rack 7, or may be programmed in the CPU or in the microcomputer 4.

During this cross-correlation process, a cross-correlation function $<S_{k-1}(x,z), S_k(x,z)>$ is maximized in order to determine the displacement undergone by each particle 5 resulting in an ultrasound echo.

Examples of such cross-correlation calculations are given in the state of the art, in particular in the following documents:

"Internal displacement and strain imaging using speckle tracking," O'Donnell et al, IEEE Transactions on Ultrasonic, Ferroelectrics, and Frequency Control, Vol. 41, Issue 3, May 1994, p. 314-325

"Elastography: A Quantitative Method for Imaging the Elasticity of Biological Tissues," Ophir et al., Ultrasonic Imaging, Vol. 13, p. 111-134, 1991, and "Pyramidal Implementation of the Lucas Kanade Feature Tracker. Description of the Algorithm," J-Y Bouguet, Intel Corp.

A displacement field is thus obtained, i.e. a set of displacement vectors or u(x,z, t) at each position (x,z) of the medium 2, which can be denoted $u_k(x,z)$ by replacing time variable t by image index k. These displacement vectors may optionally be reduced to a single component or to two or three components. In the example considered, the displacement field $u_k$ at image index k is:

$$u = \begin{bmatrix} u_x \\ u_z \end{bmatrix} \quad \text{[Math. 3]}$$

This displacement field (set of displacement vectors) is stored in the memory M or in the microcomputer 4.

An image of displacement field $Iu_k$ can be created, and all images of displacement field $Iu_k$ that represent the temporal succession of images of the medium can be visualized, in particular by means of the microcomputer screen 4*a*, e.g., as a slow-motion movie where the displacement value is shown by an optical parameter such as by a gray level or by a color level.

Determining Partial Deformation Images $I\Delta\varepsilon_k$

Partial deformations Δε may then be calculated at each point of the medium 2, i.e. vectors whose components are derivatives of the displacement vector components respectively with respect to the space variables (coordinates according to X, Z in the example considered), i.e.:

$$\Delta\varepsilon = \begin{bmatrix} \dfrac{du_x}{dx} \\ \dfrac{du_z}{dz} \end{bmatrix} \quad \text{[Math. 4]}$$

Alternatively, according to an implementation example, only the uni-axial deformation/partial deformation in Z direction is calculated. The reason for this is that the compression due to the external pressure of the probe is mainly in this direction. Similarly, in a subsequent stress calculation, only the uniaxial partial stress/stress in the Z direction is possibly calculated. This simplifies calculations.

As with displacement vectors, a partial deformation image ($I\Delta\varepsilon_k$) can be created from the set of partial deformations calculated at any point of coordinates (x,z) of the X-Z plane (image plane).

These partial deformation vectors or partial deformation images ($I\Delta\varepsilon_k$) can be displayed, in particular by means of the microcomputer screen 4*a*, as slow motion movies.

Determining Medium Movement Due to External Pressure

Deformation of the medium 2 due to variations in the external pressure P exerted on the external surface 3 is a slow, elastic, quasi-uniform deformation. This deformation propagates inside the viscoelastic medium 2, and causes the particles 5 and the elements contained in the medium 2 to move.

The external deformation caused by the external pressure P may be considered as causing movement between an image of the medium of index k ($I_k$) and a previous image of the medium of index k−1 ($I_{k-1}$).

The movement can then be determined by the displacement field ($u_k$) between an image of the medium of index k and an image of the previous medium of index k−1.

In particular, this motion can be modeled by a geometric transformation $T_k$ of index k which represents in a general and simple way the set of displacements of the displacement field at the image index k step, $u_k(x,z)$, i.e., with very few parameters, e.g., less than ten.

According to a first variant, geometric transformation $T_k$ comprises a translation, as shown between FIG. 2A and FIG. 2B.

According to a second variant, geometric transformation $T_k$ comprises a translation and a homothety.

According to a second [sic—should read "third"; translator's note] variant, geometric transformation $T_k$ comprises translation, homothety and rotation.

Thus, in the X-Z plane, the image plane, geometric transformation can be represented in matrix form as follows:

$$T_k = \begin{bmatrix} Hx \cdot \cos\theta & -Hz \cdot \sin\theta & Tx \\ Hx \cdot \sin\theta & Hz \cdot \cos\theta & Tz \\ 0 & 0 & 1 \end{bmatrix} \quad \text{[Math. 5]}$$

with the following geometric transformation (Tk) parameters:
Tx, Ty translation coefficients in the image plane,
Hx, Hz homothety coefficient in the image plane, and
θ rotation angle of axis perpendicular to the image plane.

Thus, taking three points P1, P2, and P3 of the image of respective coordinates (x1, z1), (x2, z2), (x3, z3), the following relations are obtained:

$$A = \begin{bmatrix} x1 & x2 & x3 \\ z1 & z2 & z3 \\ 1 & 1 & 1 \end{bmatrix} \quad \text{[Math. 6]}$$

$$B = \begin{bmatrix} x1+dx1 & x2+dx2 & x3+dx3 \\ z1+dz1 & z2+dz2 & z3+dz3 \\ 0 & 0 & 0 \end{bmatrix}$$

where:
dx1=$u_{x1}$ dz1=$u_{z1}$
dx2=$u_{x2}$ dz2=$u_{z2}$
dx3=$u_{x3}$ dz3=$u_{z3}$ to resume notation of the X and Z components of the displacement vectors of points P1, P2 and P3.

In addition, there is a relation that allows for the calculation of the geometric transformation $T_k$ from the previous matrices A and B, i.e., a matrix A corresponding to the coordinates of the three points in the image, and a matrix B corresponding to the coordinates of these same three points with the displacements of these points (the movement). Thus, the matrix of the geometric transformation is obtained by the matrix product of the matrix B and the inverse of the matrix A:

$$T_k = B \cdot A^{-1} \quad \text{[Math. 7]}$$

Applying this relation makes it possible to calculate the geometric transformation $T_k$ from three points P1, P2, P3.

Conversely, once the geometric transformation $T_k$ is established, this relation makes it possible to know the coordinates (x,z) of any point P by the inverse relation:

$$B = T_k \cdot A \quad \text{[Math. 8]}$$

Then, a compensation of any type of image from the previous movements can be performed by matrix multiplication of the previous geometric transformations, i.e., by matrix multiplication of the geometric transformations $T_i$, with index i varying from 1 to k.

The previous relations established with 3 points can be generalized to a point group of the image, the point group comprising 3, 4, 5 or 6 points of the image. The point group comprises between three and ten image points.

Further, in one embodiment, a population of three (of point group) image points will be taken, said population comprising a number Ng of high value point groups. For example, in this population size, the number Ng of point groups is greater than one hundred.

Therefore, the parameters of the geometric transformation $T_k$ are obtained by median values of the parameters calculated from the population of point groups of the image.

In particular, this technique can be applied to an image of the displacement field $u_k$ to deduce the motion between an image of the medium of index k and a previous image of the medium of index k−1.

By using a population of point groups, it is possible to determine a geometric transformation that represents more comprehensively the movement between the image of the medium of index k and a previous image of the medium of index k−1.

Beneficially, points in each group are selected randomly in the image. With this arrangement, a geometric transformation can be determined that more comprehensively and reliably represents the movement between images.

Determining a Shear Wave Elasticity Image of the Medium $IE_k$

The process described below is known as shear wave elasticity imaging of the medium. The temporal succession of shear wave elasticity data (or image or image data) can be used to quantify the nonlinear elasticity of the medium (as described above).

US 2005/252295 proposes an elasticity imaging technique for viscoelastic medium 2: The imaging device 1 examines the propagation of elastic shear waves in this medium. The elastic shear wave motions are monitored by the means described above, and in particular by the microcomputer 4.

This is done in several steps:
(e1.1) an excitation step during which the microcomputer 4 generates an elastic shear wave in the viscoelastic medium 2, by emitting at least one ultrasonic wave focused in the viscoelastic medium by the probe 6,
(e1.2) an observation step during which the shear wave propagation is observed simultaneously at multiple points of the observation field in the viscoelastic medium 2, this step comprising sub-steps during which multiple temporally successive intermediate images of the medium $II_{j,k}$ are generated, j being an intermediate image index comprised between 0 and M inclusive, M+1 being the number of intermediate images produced.

Each intermediate image of the medium is, for example, generated by the previously described method of determining an image of the medium $I_k$, in which at least one unfocused ultrasound compression wave burst is transmitted by the probe 6, the received acoustic signals are detected and recorded by the probe 6, and these acoustic signals are processed to create an intermediate image of the medium $(II_{j,k})$.

The focus and timing of the focused ultrasound wave transmitted in Step (e1), as well as the timing of the unfocused ultrasound waves transmitted in Step (e2), are adapted so that unfocused ultrasound waves arrive in the field of view during the propagation of the shear wave in this field of view. Thus, the shear wave is visible in the generated intermediate images of the medium $II_{j,k}$.

We then proceed to:
(e1.3) a step in which the intermediate images of the medium are processed to determine an elasticity image of the medium $IE_k$.

The intermediate images of the medium $II_{j,k}$ are processed to calculate a displacement field $u_{j,k}$, for example by correlation or cross-correlation as before. For example by cross-correlation between an intermediate image of the medium of index j $(II_{j,k})$ and the intermediate image of the medium of index j−1 $(I_{j−1,k})$. The determined displacement vectors can be used to visualize the shear wave propagation as a movie. In addition, the partial deformations Δε at each point of the medium 2 can be calculated from the displacement field.

From the displacement or deformation fields, the microcomputer 4 may then beneficially proceed to a mapping step during which, based on the evolution of the motion parameter (displacement or partial deformation) over time in the field of view, at least one shear wave propagation parameter is calculated, either at certain selected points of the field of view, or in the entire field of view.

An elasticity image $IE_k$ can then be created, corresponding to the set of shear wave propagation parameters at the various points of the field of view.

This elasticity image $IE_k$ of the medium can be viewed, in particular via the microcomputer screen 4a, where the value of the propagation parameter is illustrated by an optical parameter such as by a gray level or by a color level.

The shear wave propagation parameter that is calculated in the mapping step is selected from, for example:
the shear wave velocity Cs, or
the shear modulus μ, or
the Young's modulus E=3μ, or
the shear wave attenuation α, or
the shear elasticity μ1, or
the shear viscosity μ2, or
the mechanical relaxation time τs of the medium tissue.

For example, it is possible to calculate at different points of the field of view:
the shear wave velocity value Cs, which provides access to the hardness of the tissues,
the value of the mechanical relaxation time τs of the tissues, characteristics of the local viscosity of the medium.

For this purpose, a shear wave propagation model is used, e.g., represented by the following propagation equation, to which displacements u generated by the shear waves at each position r of the medium obey:

$$\rho \frac{\partial^2 \overline{u}(\overline{r}, t)}{\partial t^2} = c_s^2 \left(1 + \tau_s \frac{\partial \cdot}{\partial t}\right) \cdot \nabla^2 \overline{u}(\overline{r}, t) \qquad \text{[Math. 9]}$$

where
ρ is the density of the tissue
τS is the mechanical relaxation time of the tissue, and
cS is the shear wave velocity, directly related to the Young's modulus E of the tissues, using the equation:

$$c_s = \sqrt{\frac{E}{3\rho}} \qquad \text{[Math. 10]}$$

Solving this propagation equation with the set of displacements u yields the propagation parameters (cS, τS) quoted above.

Variant calculations of the propagation parameter(s) are possible. In particular, the wave equation can be solved by Fourier method, e.g., by averaging the values over a frequency band. Partial deformations may also be used instead of displacements.

Propagation parameter mappings, i.e., elasticity images, may also be established with different shear waves. It is then possible to combine them, e.g., by averaging them, in order to obtain a more accurate mapping.

The propagation speed of the shear wave in the medium 2 is sufficiently high to consider that there is no variation of the external pressure P exerted on the external surface 3 during this process during which a number of images of the medium (intermediate images) are taken to determine an elasticity image IE (propagation parameter of the shear wave). Thus, these images of the medium are not corrected by the movements of the medium.

However, the elasticity image of the medium $IE_k$ must be corrected with the motion at the considered time moment or at a close time moment (represented by index k) to be able to be compared with the image of the initial medium $I_0$, or to be able to be compared with the corrected deformation image $I\varepsilon_k^*$.

Determining an Image of a Nonlinearity Parameter $INL_k$

In a linear elastic domain, the medium 2 deforms proportionally to the stress σ and follows Hooke's law:

$$\sigma = E_0 \cdot \varepsilon \qquad \text{[Math. 11]}$$

where
$E_0$ is the Young's modulus of the linear domain, and
ε is the deformation In a nonlinear elastic domain, this proportionality is no longer valid. In most cases, the Young's modulus E of the material in medium 2 increases with compression.

The modulus of elasticity or Young's modulus E is then defined as the slope of the stress-deformation curve, i.e.:

$$E = \frac{\Delta \sigma}{\Delta \varepsilon} \qquad \text{[Math. 12]}$$

where
E is the Young's modulus,
Δσ is the local stress variation, i.e., the partial stress,
where $\Delta\varepsilon_t$ is the static elasticity quantified at moment (t) with respect to moment (t−Δt), and thus Δε is the local deformation variation, i.e. the partial deformation $\Delta\varepsilon_t$ for (Δt) tending to zero.

A nonlinearity parameter of the elasticity may for example be the Landau coefficient called the third-order elastic modulus in shear A mentioned in:

"Acoustoelasticity in soft solids: Assessment of the nonlinear shear modulus with the acoustic radiation force," Gennisson and Al., J. Acoust. Soc. Am (122), December 2007, p. 3211-3219, and "Quantitative Imaging of Nonlinear Shear Modulus by Combining Static Elastography and Shear Wave Elastography," H. Latorre-Ossa et Al., IEEE Transactions on Ultrasonics, Ferroelectrics, and Frequency Control, Vol. 51, Issue 4, p. 833-839, In particular, the equation (1) in the aforementioned document can be rewritten as a relation (R1) between elasticity (Young's modulus) E and stress σ:

$$E = E_0 - \frac{A}{\frac{4}{3}\cdot E_0}\cdot \sigma \quad [\text{Math. 13}]$$

where
E is the Young's modulus or modulus of elasticity,
$E_0$ is the Young's modulus of the linear domain, i.e., the Young's modulus of the material of the medium without compression, thus the first corrected elasticity image in the temporal succession of images
σ is the stress and for example the uniaxial $\sigma_z$ stress in the vertical Z direction, corresponding substantially to the compression induced by the external pressure exerted by the user of the probe 6, and
A is the nonlinearity parameter sought.

By differentiation of the above relation R1, the following is obtained:

$$\Delta E = -\frac{A}{\frac{4}{3}\cdot E_0}\cdot \Delta\sigma \quad [\text{Math. 14}]$$

Dividing by the Young's modulus definition of equation (eq. 1) and by integration a relation R2 is obtained between the elasticity (Young's modulus) E and the deformation ε, i.e.:

$$\ln(E) = \ln(E_0) - \frac{A}{\frac{4}{3}\cdot E_0}\cdot \varepsilon \quad [\text{Math. 15}]$$

where
E is the Young's modulus
$E_0$ is the Young's modulus of the linear domain, i.e., the Young's modulus of the material of the medium without compression, thus the first corrected elasticity image in the temporal succession of images
ln( ) is the natural logarithm function
ε is the deformation, and
A is the nonlinearity parameter to be determined.

The invention claimed is:

1. An ultrasonic method for quantifying the nonlinear shear wave elasticity of a medium, the method comprising:
collecting a temporal succession of shear wave elasticity data from the medium,
applying a variable external pressure to successively change a deformation of the medium according to a predetermined sequence of deformations during the collection of shear waves,
observing the evolution of real deformation,
quantifying the nonlinear elasticity of the medium as a function of the temporal succession of data and the evolution of deformation; and
determining a malignant nature of the medium based on the quantified nonlinear elasticity of the medium.

2. Method according to claim 1, in which observing of the evolution of real deformation is carried out in real time or in near real time.

3. Method according to claim 1, wherein applying the successively changing deformation comprises successively compressing or by successively decompressing the medium by an ultrasonic probe, the probe being simultaneously used to collect the temporal succession of data and/or to observe the evolution of real deformation.

4. Method according to claim 1, wherein observing the evolution of real deformation comprises collecting a temporal succession of ultrasound data from the medium.

5. Method according to claim 1, further comprising delivering to a user interface a level of estimated real deformation and a level of target deformation, and wherein the estimated real deformation corresponds to the observed real deformation, in particular in real-time, and the target deformation changes according to the predetermined sequence of deformations, in particular in real-time.

6. Method according to claim 5, further comprising displaying on a screen of the user interface the estimated real deformation level and the target deformation level.

7. Method according to claim 1, wherein collecting the temporal succession of the shear wave elasticity data comprises:
emitting at last one focused ultrasonic wave, thereby generating a shear wave in the medium,
acquiring a temporal succession of ultrasound data from the medium, thereby observing the shear wave propagation,
determining the elasticity data from said ultrasonic data of the medium and from a shear wave propagation model.

8. Method according to claim 1 wherein collecting the temporal succession of shear wave elasticity data and observing the successively changing deformation are set up by an ultrasound sequence by interposing shots of shear wave elasticity and static elasticity pulls, and/or said static elasticity data and said shear wave elasticity data are temporally interleaved.

9. Method according to claim 1, further comprising collecting a temporal succession of data of static elasticity ($\Delta\varepsilon_t$) of the medium
wherein observing the evolution of real deformation comprises deducing the actual deformation by the static elasticity ($\Delta\varepsilon_t$).

10. Method according to claim 9, wherein
a total static elasticity ($\varepsilon_t$) is determined based on the integration of the static elasticity values ($\Delta\varepsilon_t$), and
the real deformation is determined as a function of the total static elasticity ($\varepsilon_t$) determined.

11. Method according to claim 1 further comprising:
determining a quality parameter as a function of at least one of the following parameters: shear wave elasticity ($E_t$), static elasticity ($\Delta\varepsilon_t$) and total static elasticity ($\varepsilon_t$).

12. Method according to claim 1, further comprising:
determining a visual information representing a level of nonlinear elasticity of the medium comprising at least one image, and/or a score, and/or a symbol showing the level of nonlinear elasticity of the medium.

13. Method according to claim 9, further comprising:
presenting feedback information to a user of the probe, wherein the feedback information comprises at least one of the following:
actual deformation, quality parameter, and visual information.

14. Method according to claim 1, further comprising
determining a quality parameter as a function of at least one of the following parameters: shear wave elasticity, static elasticity and total static elasticity; and
performing a minimum number of quantifications of the nonlinear elasticity of the medium.

15. Method according to claim 1, further comprising:
collecting a temporal succession of B-mode data from the medium to calculate a compensation for movement of the medium relating to the probe, and
applying the compensation to elasticity data.

16. Method according to claim 15, wherein said B-mode data, said static elasticity data and said shear wave elasticity data are time interleaved.

17. Method according to claim 1, wherein, for at least one of the temporal succession of shear wave data, the value of a shear wave nonlinearity parameter is determined by performing a linear regression fit according to the following equation:

$$\log(E(t)) = \log(E_0) - \varepsilon \frac{3A}{4E_0}$$

where:
E(t) is the elasticity at each moment of deformation during the evolution of deformation,
$E_0$ is the elasticity at a first instant (t0),
$\varepsilon$ is the deformation, and
A is the nonlinear shear parameter.

18. Method according to claim 1, further comprising:
prior to collecting the temporal succession of shear wave elasticity data, determining at least one ultrasound or magnetic resonance imaging or mammography image or shear wave elasticity image of the medium, without applying a deformation according to a predetermined deformation sequence, and
determining a region of interest for which the nonlinear elasticity is quantified.

19. Method according to claim 1, further comprising displaying a confidence map in parallel with the display of the nonlinear elasticity image.

20. Method according to claim 1, wherein for each data or for each pixel of the image, a nonlinear elasticity value against a predefined reference value is displayed.

21. An ultrasonic method for quantifying the nonlinear shear wave elasticity of a medium using an imaging device comprising an ultrasonic probe, a microcomputer, and a user interface, the method comprising: activating a first mode of imaging of nonlinear shear wave elasticity, during which, the probe applies a variable external pressure to create a deformation of the medium according to a predetermined deformation sequence, by gradually compressing or by gradually decompressing the medium: wherein the device collects a temporal succession of ultrasound data by imaging the shear waves generated in the medium using the probe, and the device collects a temporal succession of ultrasound data, quantifying the nonlinear elasticity of the medium as a function of the temporal succession of data and the evolution of deformation observed; and determining a malignant nature of the medium based on the quantified nonlinear elasticity of the medium.

22. Method according to claim 21, further comprising, before activating the first mode:
activating a second shear wave elasticity (SWE) imaging mode,
determining at least one shear wave elasticity image of the medium by applying shear waves in the medium, without applying a deformation according to a predetermined deformation sequence,
saving the image, optionally including predefined calculations and measurements of the image, and
determining an area of interest in the image to image the nonlinear elasticity of the area.

* * * * *